US012753174B2

(12) United States Patent
Kim et al.

(10) Patent No.: US 12,753,174 B2
(45) Date of Patent: Oct. 6, 2026

(54) CRYSTALLINE FORM OF HETEROCYCLIC COMPOUND AS PROTEIN KINASE INHIBITOR

(71) Applicant: HK INNO.N CORPORATION, Chungcheongbuk-do (KR)

(72) Inventors: Young Ju Kim, Seoul (KR); Jun Kim, Seoul (KR); Hanna Kim, Seoul (KR); Jae Hong Kweon, Seoul (KR); Ye-Lim Lee, Seoul (KR); Do Seok Hwang, Seoul (KR)

(73) Assignee: HK inno.N Corporation, Chungcheongbuk-do (KR)

( * ) Notice: Subject to any disclaimer, the term of this patent is extended or adjusted under 35 U.S.C. 154(b) by 344 days.

(21) Appl. No.: 18/282,177

(22) PCT Filed: Mar. 16, 2022

(86) PCT No.: PCT/KR2022/003703
§ 371 (c)(1),
(2) Date: Sep. 14, 2023

(87) PCT Pub. No.: WO2022/197104
PCT Pub. Date: Sep. 22, 2022

(65) Prior Publication Data
US 2024/0051957 A1 Feb. 15, 2024

(30) Foreign Application Priority Data
Mar. 16, 2021 (KR) ........................ 10-2021-0034296

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC .......................... C07D 471/04; C07B 2200/13
USPC .......................................................... 546/113
See application file for complete search history.

(56) References Cited

U.S. PATENT DOCUMENTS

| | | | |
|---|---|---|---|
| 5,057,517 | A | 10/1991 | Johnston et al. |
| 7,098,333 | B2 | 8/2006 | Gillespie et al. |
| 9,133,200 | B2 | 9/2015 | Gonzalez Rodriguez et al. |
| 10,793,551 | B2 | 10/2020 | Ernst et al. |
| 10,889,586 | B2 | 1/2021 | Wu |
| 11,053,224 | B2 | 7/2021 | Liang et al. |

(Continued)

FOREIGN PATENT DOCUMENTS

| | | |
|---|---|---|
| CA | 2319275 | 8/1999 |
| CA | 2404594 | 10/2001 |

(Continued)

OTHER PUBLICATIONS

Brittain HG. 3. Preparation and Identification of Polymorphs and Solvatomorphs. InPreformulation in solid dosage form development Jan. 7, 2008 (pp. 203-246). CRC Press. (Year: 2008).*

(Continued)

*Primary Examiner* — Jeffrey S Lundgren
*Assistant Examiner* — Heather Dahlin
(74) *Attorney, Agent, or Firm* — Fish & Richardson P.C.

(57) ABSTRACT

The present invention relates to a crystalline form of the heterocyclic compound N-(4-(1-(2-cyanoacetyl)-3-methyl-1,2,3,6-tetrahydropyridin-4-yl)-1H-pyrrolo[2,3-b]pyridin-6-yl)cyclopropanecarboxamide as a protein kinase inhibitor.

4 Claims, 3 Drawing Sheets

(56) References Cited

U.S. PATENT DOCUMENTS

| | | | |
|---|---|---|---|
| 11,524,968 | B2 | 12/2022 | Lee |
| 2004/0127538 | A1 | 7/2004 | Oinuma et al. |
| 2008/0146565 | A1 | 6/2008 | Dunn et al. |
| 2014/0170110 | A1 | 6/2014 | Eastwood et al. |
| 2014/0302010 | A1 | 10/2014 | Klar et al. |
| 2016/0289207 | A1 | 10/2016 | DeMong et al. |
| 2018/0244654 | A1 | 8/2018 | Schiltz et al. |
| 2021/0171544 | A1 | 6/2021 | Lee et al. |
| 2022/0009902 | A1 | 1/2022 | Park |
| 2024/0300943 | A1 | 9/2024 | Lee et al. |

FOREIGN PATENT DOCUMENTS

| | | | | |
|---|---|---|---|---|
| CA | 2424303 | | 4/2002 | |
| CA | 2537731 | | 3/2005 | |
| CA | 2539548 | | 3/2005 | |
| CA | 2575808 | | 2/2006 | |
| CA | 2588627 | | 7/2006 | |
| CA | 2610828 | | 12/2006 | |
| CA | 2625442 | | 4/2007 | |
| CA | 2358998 | | 11/2007 | |
| CA | 2672172 | | 7/2008 | |
| CA | 2686903 | | 11/2008 | |
| CA | 2709883 | | 6/2009 | |
| CA | 2709806 | | 7/2009 | |
| CA | 2718727 | | 10/2009 | |
| CA | 2728559 | | 1/2010 | |
| CA | 2729552 | | 1/2010 | |
| CA | 2736522 | | 3/2010 | |
| CA | 2561950 | | 4/2010 | |
| CA | 2738348 | | 4/2010 | |
| CA | 2746221 | | 7/2010 | |
| CA | 2407593 | | 1/2011 | |
| CA | 2767079 | | 1/2011 | |
| CA | 2496842 | | 2/2011 | |
| CA | 2770155 | | 2/2011 | |
| CA | 2781056 | | 5/2011 | |
| CA | 2786950 | | 6/2011 | |
| CA | 2799156 | | 11/2011 | |
| CA | 2804347 | | 1/2012 | |
| CA | 2804845 | | 1/2012 | |
| CA | 2809911 | | 3/2012 | |
| CA | 2834548 | | 11/2012 | |
| CA | 2839767 | | 12/2012 | |
| CA | 2849340 | | 3/2013 | |
| CA | 2857193 | | 6/2013 | |
| CA | 2854093 | | 7/2013 | |
| CA | 2878412 | | 1/2014 | |
| CA | 2879448 | | 1/2014 | |
| CA | 2901929 | | 10/2014 | |
| CA | 2904048 | | 10/2014 | |
| CA | 2918910 | | 1/2015 | |
| CA | 2926340 | | 4/2015 | |
| CA | 2935329 | | 7/2015 | |
| CA | 2940666 | | 9/2015 | |
| CA | 2942957 | | 10/2015 | |
| CA | 2949163 | | 11/2015 | |
| CA | 2952083 | | 1/2016 | |
| CA | 2958966 | | 3/2016 | |
| CA | 2982493 | | 11/2016 | |
| CA | 2999937 | | 4/2017 | |
| CA | 3002558 | | 5/2017 | |
| CA | 3003930 | | 5/2017 | |
| CA | 3016196 | | 9/2017 | |
| CA | 3020778 | | 10/2017 | |
| CA | 2794153 | | 1/2018 | |
| CA | 3036987 | | 3/2018 | |
| CA | 3048217 | | 6/2018 | |
| CA | 3050770 | | 6/2018 | |
| CA | 3047212 | | 8/2018 | |
| CA | 2803156 | | 1/2019 | |
| CA | 3071024 | | 2/2019 | |
| CA | 3071900 | | 2/2019 | |
| CA | 3077238 | | 4/2019 | |
| CA | 3079292 | | 4/2019 | |
| CA | 3082156 | | 4/2019 | |
| CA | 3080806 | | 5/2019 | |
| CA | 3083374 | | 5/2019 | |
| CA | 3084058 | | 6/2019 | |
| CA | 3085427 | | 6/2019 | |
| CA | 3088025 | | 8/2019 | |
| CA | 3101223 | | 11/2019 | |
| CA | 3101368 | | 11/2019 | |
| CA | 3102598 | | 12/2019 | |
| CA | 3109192 | | 2/2020 | |
| CA | 3107426 | | 3/2020 | |
| CA | 3107624 | | 3/2020 | |
| CN | 102574857 | | 7/2012 | |
| CN | 103228654 | A | 7/2013 | |
| CN | 103649085 | A | 3/2014 | |
| CN | 105263930 | | 1/2016 | |
| CN | 106478651 | | 3/2017 | |
| CN | 108084153 | | 5/2018 | |
| CN | 108884080 | A | 11/2018 | |
| CN | 111372931 | A | 7/2020 | |
| EA | 14706 | | 2/2011 | |
| EA | 31882 | | 3/2019 | |
| EP | 2489663 | | 8/2012 | |
| JP | 2003523942 | | 8/2003 | |
| JP | 2005524621 | | 8/2005 | |
| JP | 2006199617 | | 8/2006 | |
| JP | 2009521504 | | 6/2009 | |
| JP | 2010511655 | | 4/2010 | |
| JP | 2012532152 | | 12/2012 | |
| JP | 2014509625 | | 4/2014 | |
| JP | 2015522620 | | 8/2015 | |
| JP | 2016516791 | | 6/2016 | |
| JP | 2018529770 | | 10/2018 | |
| JP | 2021500339 | | 1/2021 | |
| KR | 10-2014-0004637 | | 1/2014 | |
| KR | 10-2014-0027318 | | 3/2014 | |
| KR | 10-2019-0039823 | | 4/2019 | |
| KR | 10-2019-0043437 | | 4/2019 | |
| KR | 10-2019-0068626 | | 4/2019 | |
| KR | 20190043437 | A * | 4/2019 | ........... C07D 471/04 |
| RU | 2485106 | | 6/2013 | |
| RU | 2016104388 | | 8/2017 | |
| RU | 2662810 | C2 | 7/2018 | |
| WO | WO 2001000213 | | 1/2001 | |
| WO | WO 2002055084 | | 7/2002 | |
| WO | WO 2002083648 | | 10/2002 | |
| WO | WO 2007004944 | | 1/2007 | |
| WO | WO 2007070589 | | 6/2007 | |
| WO | WO 2008079907 | | 7/2008 | |
| WO | WO 2008090181 | | 7/2008 | |
| WO | WO 2008135785 | | 11/2008 | |
| WO | WO 2009027732 | | 3/2009 | |
| WO | WO 2009049028 | | 4/2009 | |
| WO | WO 2009131687 | | 10/2009 | |
| WO | WO 2010068806 | | 6/2010 | |
| WO | WO 2011003418 | | 1/2011 | |
| WO | WO 2011005119 | | 1/2011 | |
| WO | WO 2011163424 | | 12/2011 | |
| WO | WO 2012020787 | | 2/2012 | |
| WO | WO 2012069202 | | 5/2012 | |
| WO | WO 2013020369 | | 2/2013 | |
| WO | WO 2014071031 | | 5/2014 | |
| WO | WO 2014075318 | | 5/2014 | |
| WO | WO 2014137728 | | 9/2014 | |
| WO | WO 2014170248 | | 10/2014 | |
| WO | WO 2015006754 | | 1/2015 | |
| WO | WO 2015187684 | | 12/2015 | |
| WO | WO 2015192119 | | 12/2015 | |
| WO | WO 2016183094 | | 11/2016 | |
| WO | WO 2017050938 | | 3/2017 | |
| WO | WO 2017087905 | | 5/2017 | |
| WO | WO 2017098467 | | 6/2017 | |
| WO | WO 2017161004 | | 9/2017 | |
| WO | WO 2018108079 | A1 | 6/2018 | |

(56) References Cited

FOREIGN PATENT DOCUMENTS

| | | |
|---|---|---|
| WO | WO 2018154578 | 8/2018 |
| WO | WO 2019078619 | 4/2019 |

OTHER PUBLICATIONS

Bhattacharya S, Brittain HG, Suryanarayanan R. Thermoanalytical and crystallographic methods. InPolymorphism in pharmaceutical solids Nov. 12, 2018 (pp. 330-358). CRC Press. (Year: 2018).*
International Preliminary Report on Patentability in International Appln. No. PCT/KR2022/003703, mailed on Sep. 12, 2023, 11 pages (with Machine translation).
International Search Report and Written Opinion in International Appln. No. PCT/KR2022/003703, mailed on Jun. 27, 2022, 17 pages (with English translation).
Office Action in Chinese Appln. No. 202280021505.9, mailed on Jul. 29, 2025, 13 pages (with English translation).
Fundamentals of Medical Prophylaxis: Educational and Methodical Manual for Students and Cadets of Advanced Training Cycles of States Professional Educational Institutions, Boytsov et al. (Reviewers), Novosibirsk, 2016, pp. 13-21 (22 pages in total with machine translation).
Gupta et al., "Salts of Therapeutic Agents: Chemical, Physicochemical, and Biological Considerations," Molecules, Jul. 14, 2018, 23(7), 1719, pp. 1-15.
Mordasova et al., "Efficacy of tofacitinib in the treatment of ulcerative colitis with moderate and severe course," Effective Pharmacotherapy, 2021, 17(16):56-60 (10 pages in total with machine translation).
Novikova et al., "Autoimmune diseases: diagnostics and principles of therapy: a tutorial," 2017, pp. 18 and 22 (8 pages in total with machine translation).
Office Action in Chinese Appln. No. 202280021504.4, mailed on Jul. 28, 2025, 14 pages (with English translation).
Office Action in Russian Appln. No. 2023126285/04(058073), mailed on Jun. 20, 2025, 27 pages (with English translation).
Sarma et al., "Solid formation of pharmaceuticals: Polymorphs, salt and cocrystals," Korean J. Chem. Eng., 2011, 28(2):315-322.
U.S. Appl. No. 16/757,182 (U.S. Pat. No. 11,524,968), filed Apr. 17, 2020 (Dec. 13, 2022), Hyuk Woo Lee.
U.S. Appl. No. 17/294,226 (U.S. Pat. No. 12,180,185), filed May 14, 2021 (Dec. 31, 2024), Ji-Yeon Park.
U.S. Appl. No. 18/282,182, filed Sep. 14, 2023, Juhyun Lee.
Anderson et al., "Chapter 34: Preparation of water-soluble organic compound by salt formation", The Practice of Medicinal Chemistry, Wermuth (ed.), Technomics, Inc., Sep. 25, 1999, pp. 347-365 (with Machine translation, 39 pages in total).
AU Office Action in Australian Appln. No. 2018353759, dated Apr. 26, 2022, 10 pages.
AU Office Action in Australian Appln. No. 2018353759, dated Jun. 23, 2021, 8 pages.
AU Office Action in Australian Appln. No. 2022237154, mailed on Jun. 17, 2024, 2 pages.
AU Office Action in Australian Appln. No. 2022239128, mailed on Apr. 22, 2024, 2 pages.
Bastin et al., "Salt Selection and Optimisation Procedures for Pharmaceutical New Chemical Entities," Organic Process Research & Development, Sep. 2000, 4(5):427-435.
Belikov et al., "The Relationship Between a Chemical Structure and Properties of Substances and their Action to Organism," Pharmaceutical Chemistry, Moscow Publishing House, MEDpress-inform, 2007, Section 2.6, pp. 27-29.
Belikov et al., "The Relationship Between the Structure of Molecules of Substances and their Effect on the Body", Pharmaceutical Chemistry, Chapter 2.2, 1993, pp. 43-47 (with English abstract).
Bernshtein, "Molecular crystal polymorphism," Moscow Science, 2007, Chapter 7.3.2 Bioavailability, pp. 324-330 (with English translation, 13 pages in total).
Brown (ed), "Biososteres in Medicinal Chemistry", 2010, 242 pages.
CA Office Action in Canadian Appln. No. 3082156, dated Jun. 11, 2021, 6 pages.
CA Office Action in Canadian Appln. No. 3212253, mailed on Oct. 4, 2024, 3 pages.
CA Office Action in Canadian Appln. No. 3212256, mailed on Oct. 4, 2024, 4 pages.
Caira, "Crystalline Polymorphism of Organic Compounds," Topics in Current Chemistry, 1998, 198:163-208 (p. 164, section 3.1, p. 188).
CN Office Action in Chinese Appln. No. 201880067864.1, dated Jan. 11, 2022, 19 pages (with English Translation).
Durnov et al., "Pediatric Oncology", Second Edition Medicina, 2003, pp. 139 (with English abstract).
Dyson et al., "Chemistry of Synthetic Drug Substances", MIR, 1964, pp. 12-19 (with English Abstract).
EP Search Report in a European Appln. No. 18869085.3, dated Nov. 16, 2022, 7 pages.
EP Search Report in a European Appln. No. 19885184.2, dated Jun. 24, 2022, 7 pages.
Experimental Chemistry Courses (Secondary) (Jikken Kagaku Kouza (Zoku)), "Separation and Purification", The Chemical Society of Japan (ed.), Maruzen Co., Ltd., Jan. 25, 1967, pp. 159-178, 186-187 (with Machine translation, 45 pages in total).
Golub et al., "Molecular Classification of Cancer: Class Discovery and Class Prediction by Gene Expression Monitoring", Science, 1999, 286:531-537.
Gurzov et al., "The JAK/STAT Pathway in Obesity and Diabetes", The FEBS Journal, 2016, 283:3002-3015.
ID Office Action in Indonesian Appln. No. P00202003535, dated Jun. 30, 2022, 4 pages (with English Translation).
ID Office Action in Indonesian Appln. No. P00202104463, dated Jul. 18, 2022, 6 pages (with English Translation).
IN Examination Report in Indian Appln No. 202137026444, dated Aug. 13, 2021, 5 pages (with English Translation).
IN Hearing Notice in Indian Appln. No. 202137026444, dated Mar. 25, 2022, 3 pages (with English Translation).
International Preliminary Report on Patentability in International Appln. No. PCT/KR2022/003702, mailed on Sep. 12, 2023, 14 pages (with English Translation).
International Search Report and Written Opinion in International Appln. No. PCT/KR2022/003702, mailed on Jun. 27, 2021, 21 pages (with English Translation).
International Search Report for International Appln. No. PCT/KR2018/012270 mailed on Feb. 1, 2019. 4 pages.
International Search Report in International Appln. No. PCT/KR2019/015516, dated Mar. 9, 2020, 3 pages.
Jones et al., "Design and Synthesis of a pan-Janus Kinase Inhibitor Clinical Candidate (PF-06263276) Suitable for Inhaled and Topical Delivery for the Treatment of Inflammatory Diseases of the Lungs and Skin," Just-Accepted Manuscript, Journal of Medicinal Chemistry, 2016, 63 pages, DOI:10.1021/acs.jmedchem.6b01634.
JP Office Action in Japanese Appln. No. 2020-521905, dated Apr. 27, 2021, 15 pages (with English Translation).
JP Office Action in Japanese Appln. No. 2020-521905, dated Nov. 2, 2021, 8 pages (with English Translation).
JP Office Action in Japanese Appln. No. 2021-526602, dated Jun. 7, 2022, 5 pages (with English Translation).
JP Office Action in Japanese Appln. No. 2023-556847, mailed on Jul. 23, 2024, 11 pages (with English translation).
JP Office Action in Japanese Appln. No. 2023-556851, mailed on Aug. 27, 2024, 8 pages (with English translation).
Kasatkina et al., "Protein Kinases: Variety and Classification", Transduction of Hormonal Signal, Research Work, 2014 (with English abstract).
Kiselgof et al., "6-(2-Furanyl)-9H-purin-2-amine derivatives as $A_{2A}$ adenosine antagonists," Bioorganic & Medicinal Chemistry Letters. 2005, 15:2119-2122.
Kontzias et al. "Jakinibs: A New Class of Kinase Inhibitors in Cancer and Autoimmune Disease", Current Opinion in Pharmacology, 2012, 12:464-470.

(56) References Cited

OTHER PUBLICATIONS

KR Office Action for App No. KR 10-2017-0135515, dated Nov. 1, 2018 (with English translation) (21 pages).
KR Office Action for App No. KR 10-2018-0140578, dated Mar. 25, 2020 (with English Translation) 11 pages.
KR Office Action for App No. KR 10-2019-0064740, dated Jan. 2, 2020 (English translation) (15 pages).
KR Office Action for App No. KR 10-2019-0064740, dated Jul. 1, 2020 (English translation) (5 pages).
KR Office Action for App No. KR 10-2019-0098472, dated May 4, 2020 (English translation) (5 pages).
Kuznetsova, "Guidelines," Irkutsk State University (GOVPOIGU), Department of General Physics, 2005, p. 3, 2nd Paragraph.
Lacroix et al ., "Identification of Novel Smoothened Ligands Using Structure-Based Docking", PLOS One, 2016, vol. 11, No. 8 , e0160365, Internal pp. 1-20.
Li et al., "Design and optimization of (3-aryl-1H-indazol-6-yl)spiro[cyclopropane-1,3'-indolin]-2'-ones as potent PLK4 inhibitors with oral antitumor efficacy," Bioorganic & Medicinal Chemistry Letters, 2016, 26(19):4625-4630, DOI:10.1016/j.bmcl.2016.08.063 (Accepted Manuscript, 16 pages).
Lucas et al., "4-Acyl Pyrroles: Mimicking Acetylated Lysines in Histone Code Reading", Angew. Chem. Int. Ed., 2013, vol. 52, pp. 14055-14059, 6 pages.
Mit'kina et al., "Stress studies and photostability as a part of pharmaceutical drug development data," The Bulletin of the Scientific Centre for Expert Evaluation of Medicinal Products, 2015, (2):9-12, 11 pages (with English Translation).
MX Office Action in Mexican Appln. No. MX/a/2020/003868, dated Jun. 21, 2022, 18 pages (with English Translation).
New and Pharmaceutical Examination (Shin-Yakuzaigaku), The Third Revised Edition, Okano (ed.), Nankaido Co., Ltd., Apr. 10, 1987, p. 111 (with Machine translation, 5 pages in total).
New Pharmaceutical Preparation (Shin-Seizaigaku), Nakai et al. (ed), Nanzando Co., Ltd., Apr. 25, 1984, pp. 102-103, 232-233 (with Machine translation, 12 pages in total).
Nicolas et al., "The Role of JAK-STAT Signaling Within the CNS" Landes Bioscience, 2013, 2(1):122925, 10 pages.
Ooshima, "Crystallization of Polymorphs and Pseudo-polymorphs and Its Control," Pharm Stage, Jan. 15, 2007, 6(10):48-53 (with Machine translation, 22 pages in total).
Pala et al., "Virtual Screening and Biological Validation of Novel Influenza Virus PA Endonuclease Inhibitors", ACS Med. Chem. Lett., Aug. 2015, 6(8):866-871 (7 pages).
Polymorphism and Crystallization of the Pharmaceutical Drugs, Ashizawa (ed.), Maruzen Planet Co. Ltd., Sep. 20, 2002, pp. 3-16, 273-278 (with Machine translation, 40 pages in total).
PubChem CID 11020179, National Center for Biotechnology Information, PubChem Compound Summary for CID 11020179, 6-Phenyl-7H-purin-2-amine, https://pubchem.ncbi.nlm.nih.gov/compound/6-Phenyl-7H-purin-2-amin, accessed Jun. 21, 2021, create date Oct. 26, 2006, 12 pages.
Rituraj et al., "Schizophrenia: A Look Forward with Zinc06025953", International Journal of Pharmaceutical Sciences and Research, 2017, 8(5):2122-2133.
Rodriguez-Spong et al., "General principles of pharmaceutical solid polymorphism: a supramolecular perspective," Adv Drug Deliv Rev, Feb. 23, 2004, 56(3):241-274.
RU Office Action and Search Report in Russian Appln. No. 2023126280/04(058068), mailed on Apr. 15, 2024, 31 pages (with English translation).
RU Office Action and Search Report in Russian Appln. No. 2023126285/04(058073), mailed on Apr. 4, 2024, 23 pages (with English translation).
RU Office Action for App No. 2020115890/04, dated Oct. 15, 2020 (English translation) (25 pages).
RU Office Action in Russian Appln. No. 2020115890/04(026059), dated Apr. 29, 2021, 29 pages with English Translation.
RU Office Action in Russian Appln. No. 2021117137/04(036124), dated Mar. 17, 2022, 22 pages (with English Translation).
RU Search Report for App No. RU2020115890/04, dated Oct. 8, 2020, 5 pages (with English translation).
Saal et al., "Pharmaceutical salts: A summary on doses of salt formers from the Orange Book," European Journal of Pharmaceutical Sciences, Jun. 2013, 49(4):614-623 (pp. 614-161 "Introduction").
Sarma et al., "Solid forms of pharmaceuticals: Polymorphs, salts and cocrystals," Korean J Chem Eng, Jan. 31, 2011, 28(2):315-322 (p. 316, left colum lines 6-17).
Shahani et al., "A 2,6,9-hetero-trisubstituted purine inhibitor exhibits potent biological effects against multiple myeloma cells," Bioorganic & Medicinal Chemistry, 2013, 21:5618-5628.
Shahani et al., "A 2,6,9-hetero-trisubstituted purine inhibitor exhibits potent biological effects against multiple myeloma cells," with Supporting Information, Bioorganic & Medicinal Chemistry, 2013, 21:5618-5628 (100 pages including the supplemental material).
Sharma et al., "Polymorphism in pharmaceutical compounds," Advances and Futuristic Trends in Material Science, 2011, pp. 39-48 (part 5, p. 43-44).
Smirnova et al., "Chapter 11.2 Relationship of crystal structure of substance, pharmacokinetics and efficacy of drug," Clinical pharmacokinetics: theoretical, applied and analytical aspects: a manual, (edited by Kukes), 2009, pp. 235-248 (with Machine translation).
Stepkowski et al., Selective inhibitor of Janus tyrosine kinase 3, PNU156804, prolongs allograft survival and acts synergistically with cyclosporine but additively with rapamycin, Blood, 2002, vol. 99 (2), p. 680-689.
Takata, "API Form Screening and Selection in the Drug Discovery Stage", Pharm Stage, Jan. 15, 2007, 6(10):20-25 (with Machine translation, 19 pages in total).
The Ministry of Health, Labour and Welfare (Japan), "The Japanese Pharmacopoeia," 16th edition, 2011, pp. 64-68 and p. 2070 (with corresponding English pp. 74-80 and 2253-2255), 19 pages in total.
Tsrigotis et al., "Treatment of Experimental Candia Sepsis with a Janus Kinase Inhibitor Controls Inflammation and Prolongs Survival", Antimicrobial Agents and Chemotherapy, Dec. 2015, 59(12):7367-7373.
Tyukavkina et al., "Biorganic Chemistry, published by Drofa", Moscow, 2005, pp. 83-85 (with English abstract).
Variankaval et al., "From form to function: Crystallization of active pharmaceutical ingredients," AIChE Journal, Jul. 2008, 54(7):1682-1688 (c. 1682 "Crystal Form").
Yamano, "Approach to Crystal Polymorph in Process Research of New Drug", Journal from the Society of Synthetic Organic Chemistry, Sep. 2007, 65(9):907-913 (with Machine translation, 21 pages in total).
U.S. Appl. No. 16/757,182, filed Apr. 17, 2020, Lee et al.
U.S. Appl. No. 17/294,226, filed May 14, 2021, Park et al.
U.S. Appl. No. 18/282,182, filed Sep. 14, 2023, Lee et al.

* cited by examiner

CRYSTALLINE FORM OF HETEROCYCLIC COMPOUND AS PROTEIN KINASE INHIBITOR

TECHNICAL FIELD

The present invention relates to a novel crystalline form of a heterocyclic compound as a protein kinase inhibitor and a preparation method thereof.

BACKGROUND

In general, it is obvious that the same drug may show a difference in pharmaceutically important properties such as solubility or dissolution properties and bioavailability in each form such as a noncrystalline form, one or more crystalline forms, salts, and the like. In selecting the noncrystalline and crystalline forms, the noncrystalline form has high solubility, and thus has advantages in increasing drug efficacy and exhibiting a rapid action, but has disadvantages in being unstable, having a short shelf life, and having difficulty to control a release rate and a blood concentration of a drug. On the contrary, the crystalline form has low solubility and thus has low bioavailability per unit weight, but has an advantage in preparing a formulation capable of securing stability and continuous release. As such, since the crystalline form is stable, but has low solubility compared to the noncrystalline form, the solubility needs to be sacrificed when preferentially considering stability. On the contrary, there is a dilemma in which the stability needs to be sacrificed when preferentially considering the solubility, and thus it is very difficult to obtain a crystal which satisfies both stability and solubility at the same time.

Janus kinase (JAK) is an enzyme which controls various intracellular processes by phosphorylating other proteins to regulate the activity, position, and function of the proteins. The Janus kinase is located at an intracellular receptor of an inflammatory cytokine, and the inflammatory cytokine binds with the receptor, phosphorylates, and transmits a signal of the inflammatory cytokine into cells through an action with STAT molecules. An excessive activation of signal transduction through such various inflammatory cytokines causes an immune system of our body to attack the body and thus leads to the occurrence of autoimmune diseases. In recent years, it has been reported that JAK1 inhibitors rapidly ameliorate the severity and symptoms of Alzheimer's disease in phase II and phase III clinical trials on selective JAK1 inhibitors, upadasitinib and abrocitinib.

DETAILED DESCRIPTION OF THE INVENTION

Technical Problem

One object of the present invention is to provide a novel crystalline form of a heterocyclic compound as a protein kinase inhibitor.

Other object of the present invention is to provide a method for preparing the crystalline form.

Technical Solution

The inventors of the present application have made efforts to discover a compound having improved physicochemical properties, capable of minimizing the occurrence of related materials by enhancing stability against heat and moisture, while having a pharmacological activity equal to or higher than that of an existing compound, and thus have identified a crystalline form of a heterocyclic compound according to the present invention, thereby completing the present invention.

In the crystalline form of the heterocyclic compound as a protein kinase inhibitor according to the present invention, the heterocyclic compound is represented by formula I below.

[Formula I]

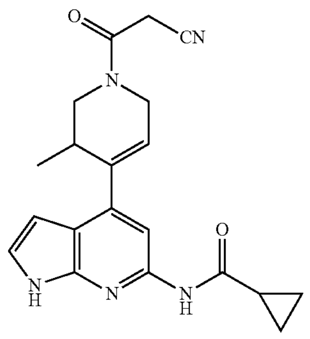

The name of the heterocyclic compound represented by above formula I is N-(4-(1-(2-cyanoacetyl)-3-methyl-1,2,3,6-tetrahydropyridin-4-yl)-1H-pyrrolo[2,3-b]pyridine-6-yl)cyclopropanecarboxamide.

The heterocyclic compound represented by above formula I may be represented by each of (S)—N-(4-(1-(2-cyanoacetyl)-3-methyl-1,2,3,6-tetrahydropyridin-4-yl)-1H-pyrrolo[2,3-b]pyridine-6-yl)cyclopropanecarboxamide and (R)—N-(4-(1-(2-cyanoacetyl)-3-methyl-1,2,3,6-tetrahydropyridin-4-yl)-1H-pyrrolo[2,3-b]pyridin-6-yl)cyclopropanecarboxamide, or may be a mixture thereof.

In one embodiment, the heterocyclic compound of the present invention or pharmaceutically acceptable salts thereof may be a compound represented by formula II below or pharmaceutically acceptable salts thereof.

[Formula II]

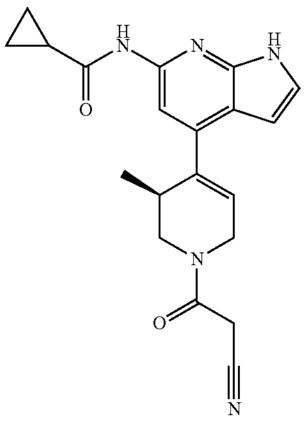

The name of the heterocyclic compound represented by above formula II is (S)—N-(4-(1-(2-cyanoacetyl)-3-methyl-1,2,3,6-tetrahydropyridin-4-yl)-1H-pyrrolo[2,3-b]pyridin-6-yl)cyclopropanecarboxamide.

A powder X-ray diffraction (XRD) pattern of the crystalline form according to the present invention includes diffraction peaks at diffraction angle 2θ (±0.2°) values of 4.6°, 8.1°, and 11.2°.

The powder X-ray diffraction (XRD) pattern may further include at least one of diffraction peaks at diffraction angle 2θ (±0.2°) values of 8.8°, 15.5°, and 20.3°.

The powder X-ray diffraction (XRD) pattern includes diffraction peaks at diffraction angle 2θ (±0.2°) values of 4.6°, 8.1°, 8.8°, 11.2°, 15.5° and 20.3°.

In one embodiment, the powder X-ray diffraction (XRD) pattern may include diffraction peaks at diffraction angle 2θ (±0.2°) values of 4.6°, 8.1°, 8.8°, 11.2°, 12.1°, 15.5°, 20.3° and 22.40.

The crystalline form according to the present invention has a mass reduction rate of 1.6% at 150° C. as a result of thermogravimetric analysis (TGA).

The crystalline form according to the present invention shows a differential scanning calorimetry (DSC) endothermic peak at 142.07 to 157.29° C. In this case, the differential scanning calorimetry endothermic peak may appear when a temperature rising rate is 10° C./min.

(1) There may be provided a crystalline form of N-(4-(1-(2-cyanoacetyl)-3-methyl-1,2,3,6-tetrahydropyridin-4-yl)-1H-pyrrolo[2,3-b]pyridin-6-yl)cyclopropanecarboxamide, in which the X-ray powder diffraction pattern includes diffraction peaks at diffraction angle 2θ (±0.2°) values of 4.6°, 8.10 and 11.2°.

(2) There may be provided the crystalline form according to above (1), in which the X-ray powder diffraction pattern further includes at least one of diffraction peaks at diffraction angle 2θ (±0.2°) values of 8.8°, 15.5°, and 20.3°.

(3) There may be provided the crystalline form according to above (1) or (2), in which the X-ray powder diffraction pattern includes diffraction peaks at diffraction angle 2θ (±0.2°) values of 4.6°, 8.1°, 8.8° and 11.2°.

(4) There may be provided the crystalline form according to above (1), (2) or (3), in which the crystalline form includes a mass reduction rate of 1.6% at 150° C. as a result of thermogravimetric analysis (TGA).

(5) There may be provided the crystalline form according to above (1), (2), (3) or (4), in which the crystalline form shows a differential scanning calorimetry (DSC) endothermic peak at 142.07 to 157.29° C.

The crystalline form of the heterocyclic compound according to the present invention may be prepared by the following method, which includes:

(A) mixing N-(4-(1-(2-cyanoacetyl)-3-methyl-1,2,3,6-tetrahydropyridin-4-yl)-1H-pyrrolo[2,3-b]pyridin-6-yl) cyclopropanecarboxamide, which is a heterocyclic compound represented by formula I according to the present invention, with an organic solvent, water or a mixture thereof, and (B) stirring the resulting product obtained in above (A) to precipitate crystals.

The resulting product obtained in above (A) may be a solution in which N-(4-(1-(2-cyanoacetyl)-3-methyl-1,2,3,6-tetrahydropyridin-4-yl)-1H-pyrrolo[2,3-b]pyridin-6-yl) cyclopropanecarboxamide is dissolved in an organic solvent, water or a mixture thereof, or a suspension in which N-(4-(1-(2-cyanoacetyl)-3-methyl-1,2,3,6-tetrahydropyridin-4-yl)-1H-pyrrolo[2,3-b]pyridin-6-yl)cyclopropanecarboxamide is suspended in an organic solvent, water or a mixture thereof.

The organic solvent used in above (A) may be ethyl acetate, ethyl formate, dichloromethane, acetone, methanol, ethanol, isopropanol, acetonitrile, toluene, tert-butyl methyl ether, 2-butanone, or a mixture thereof.

Above (B) may be performed to cool down or heat the mixed solution to be stirred.

The preparation method may further include (C) adding an anti-solvent to mature crystals, after the precipitating of the crystals of above (B). In this case, the anti-solvent may be water, hexane, heptane, tert-butyl methyl ether, isopropyl ether, cyclohexane, or a mixture thereof.

Advantageous Effects

A crystalline form of the heterocyclic compound represented by formula I according to the present invention has excellent physical stability and thus can be advantageously used in formulating medicines.

BEST MODE FOR INVENTION

Figure 1:
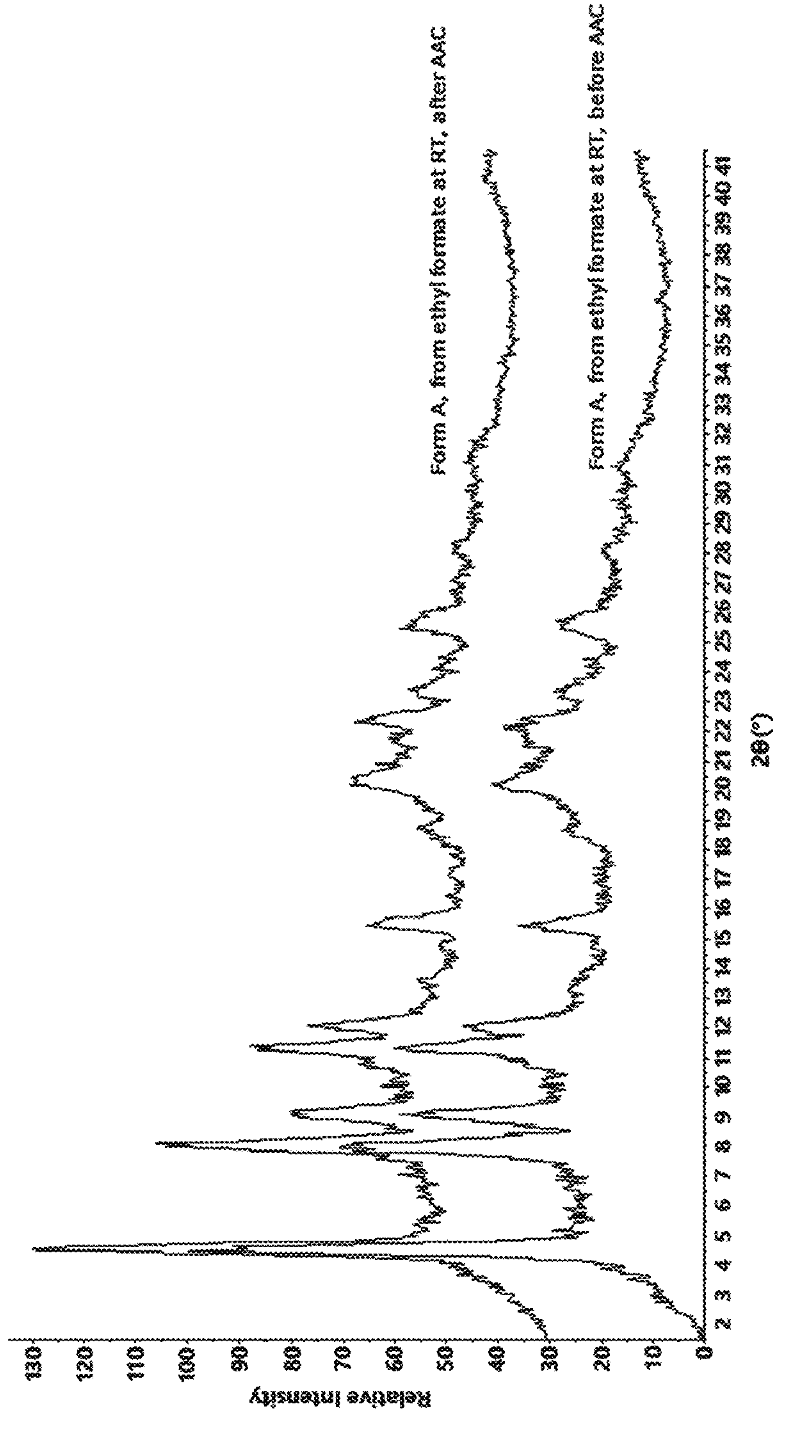
FIG. 1 is a graph showing the results of XRPD analysis before and after exposure of the crystalline form of the present invention to stress conditions.

Hereinafter, the present invention will be described with reference to examples. All the terms used herein including technical or scientific terms have the same meaning as commonly understood by those ordinary skilled in the art, to which the present invention pertains, unless defined otherwise. Such terms as those defined in a generally used dictionary are to be interpreted to have the meanings equal to the contextual meanings in the relevant art, and are not to be interpreted to have ideal or excessively formal meanings, unless clearly defined in the present application.

Preparing Example 1: Synthesis of (S)—N-(4-(1-(2-cyanoacetyl)-3-methyl-1,2,3,6-tetrahydropyridin-4-yl)-1H-pyrrolo[2,3-b]pyridin-6-yl)cyclopropanecarboxamide The title compound was prepared according to the method disclosed in Korean Unexamined Patent Application No. 2019-0043437.

$^1$H NMR (400 MHz, DMSO-$d_6$) δ 11.44 (s, 1H), 10.57 (s, 1H), 7.84 (d, J=10.2 Hz, 1H), 7.34 (d, J=3.1 Hz, 1H), 6.48 (dd, J=1.8, 3.7 Hz, 1H), 6.17-6.03 (m, 1H), 4.31-4.01 (m, 6H), 3.96-3.62 (m, 2H), 3.02 (m J=36.6 Hz, 1H), 2.02 (s, 1H), 0.88 (s, 3H), 0.84-0.73 (m, 4H); MS(ESI+) m/z 364 $(M+H)^+$

Example 1: Preparation of Crystalline Form A 32 mg of the compound according to formula II obtained in Preparation Example 1 was mixed with 100 mL of ethyl formate to obtain a suspension. The suspension was continuously stirred at room temperature for 24 hours, centrifuged to obtain a solid, and vacuum-dried (30° C., 10 mbar) to obtain a solid product.

Example 2: Preparation of Crystalline Form A

In addition, 32 mg of the compound according to formula II obtained in Preparation Example 1 was mixed with 100 mL of acetonitrile to obtain a suspension. The suspension was continuously stirred at room temperature for 24 hours, centrifuged to obtain a solid, and vacuum-dried (30° C., 10 mbar) to obtain a solid product.

Analysis and Measurement Method

1. XRPD Analysis A plate for obtaining an XRPD pattern was mounted on a Bruker General Area Detector Diffraction System (GADDS) equipped with a VANTEC-500 gas domain detector calibrated for intensity and geometric changes. Calibration of measurement accuracy (peak position) was performed using NIST SRM1976 standard (Corundum). Data collection was performed at room temperature using monochromatic CuKα radiation in a diffraction angle (2θ) region of 1.5° to 41.5°, the most distinct part of the XRPD pattern. The diffraction pattern of each well was collected at two 2θ ranges (1.5°≤2θ≤21.5° for a first frame and 9.5°≤2θ≤41.5° for a second frame) with an exposure time of 90 seconds for each frame. No background subtraction or curve smoothing was applied to the XRPD pattern. The carrier material used in the XRPD analysis was transparent to X-rays.

2. DSC Analysis

Melt properties were obtained from DSC thermograms recorded with a heat flux DSC822e apparatus (product name, Mettler-Toledo GmbH, Switzerland). DSC822e corrected temperature and enthalpy with a small indium piece (melting point at 156.6° C.; ΔHf=28.45 J/g). A sample was sealed in a standard 40 μL aluminum pan, followed by drilling a pin-hole therein, and then heated from 25° C. to 300° C. in a DSC at a heating rate of 10° C./min. Dry $N_2$ gas was used at a flow rate of 50 mL/min to purge a DSC equipment during the measurement.

3. TGA/SDTA and TGMS Analysis

A mass loss caused by solvent or a moisture loss from crystals was determined by thermogravimetric analysis/simultaneous differential thermal analysis (TGA/SDTA). A weight versus temperature curve was generated by monitoring the weight of samples during heating in a TGA/SDTA851e apparatus (product name, Mettler-Toledo GmbH, Switzerland). TGA/SDTA851e was calibrated with indium and aluminum samples. The sample was placed in a 100 μL aluminum crucible and sealed, and then a pin-hole was drilled therein. The crucible was heated from 25° C. to 300° C. in TGA at a heating rate of 10° C./min. Dry $N_2$ gas was used for purging. The gas coming out of the TGA sample was analyzed by Omnistar GSD 301 T2 (product name, Pfeiffer Vacuum GmbH, Germany), which was a quadrupole mass spectrometer for analyzing a mass in the range of 0-200 amu.

4. Experiment on Physical Stability Evaluation

Samples were packaged in the form of ((LPDE+N2)+silica gel 1 g+LDPE)+Al-Bag, and stored under stress conditions (60° C.±2° C./80% RH±5%) for two days before evaluation.

Analysis/Measurement/Evaluation Results

1. Results of XPRD Analysis and Stability Evaluation on Crystalline Form

The crystalline forms obtained according to Examples 1 and 2 were subjected to an XPRD analysis method as described above to obtain a XPRD analysis graph. The results thereof were shown in FIG. 1. As a result of XPRD obtained in FIG. 1, diffraction angles are shown in Table 1 below.

TABLE 1

| Diffraction angle (2θ, unit: °) | Relative intensity |
|---|---|
| 4.6 | Strong |
| 8.1 | Strong |
| 8.8 | Moderate |
| 11.2 | Strong |
| 12.1 | Moderate |
| 15.5 | Moderate |
| 20.3 | Moderate |
| 22.4 | Moderate |

Referring to FIG. 1 and Table 1, it can be confirmed that the crystalline forms obtained according to Examples 1 and 2 show diffraction peaks having dominant intensity at specific diffraction angles and accordingly, it is proved that they are not amorphous but crystalline forms.

In particular, referring to FIG. 1, it can be confirmed that even when the crystalline forms obtained according to Examples 1 and 2 are placed under stress conditions, there is substantially no change in the XPRD pattern before/after the stress conditions. Accordingly, it can be seen that the crystalline form according to the present invention has excellent physical stability and thus long-term storage stability is secured.

2. Results of DSC Analysis on Crystalline Form

The crystalline forms obtained according to Examples 1 and 2 were subjected to a DSC analysis method as described above to obtain a DSC analysis graph. The results thereof were shown in FIG. 2.

Figure 2:
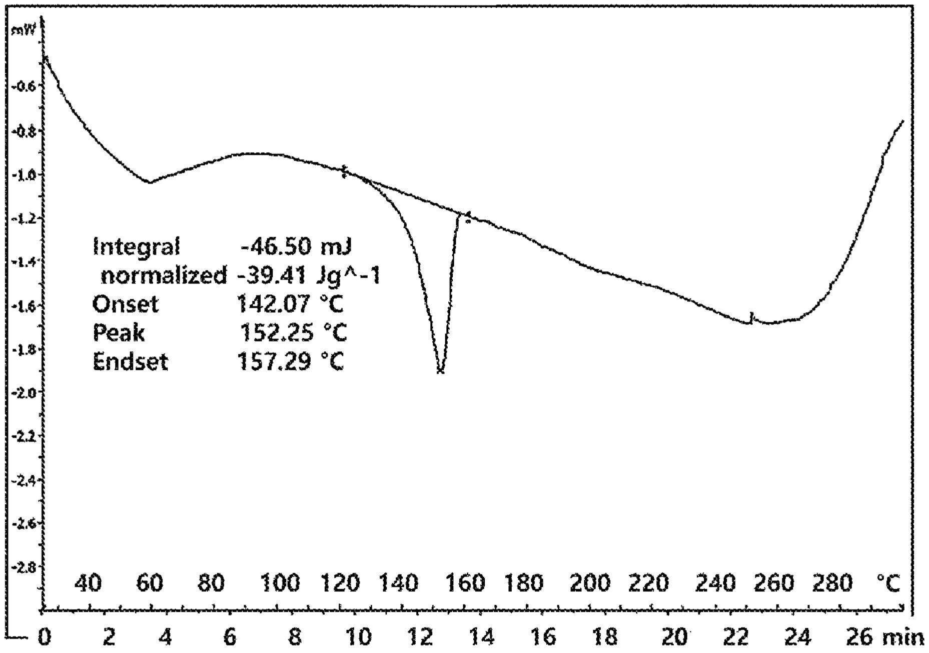
FIG. 2 is a view showing the results of DSC analysis on the crystalline form of the present invention.

Referring to FIG. 2, the crystalline form according to the present invention shows a differential scanning calorimetry (DSC) endothermic peak at 142.07 to 157.29° C.

3. Results of TGMS Analysis on Crystalline Form

The crystalline forms obtained according to Examples 1 and 2 were subjected to a TGA/SDTA and TGMS analysis method as described above to obtain a TGMS analysis graph. The results thereof were shown in FIG. 3.

Figure 3:
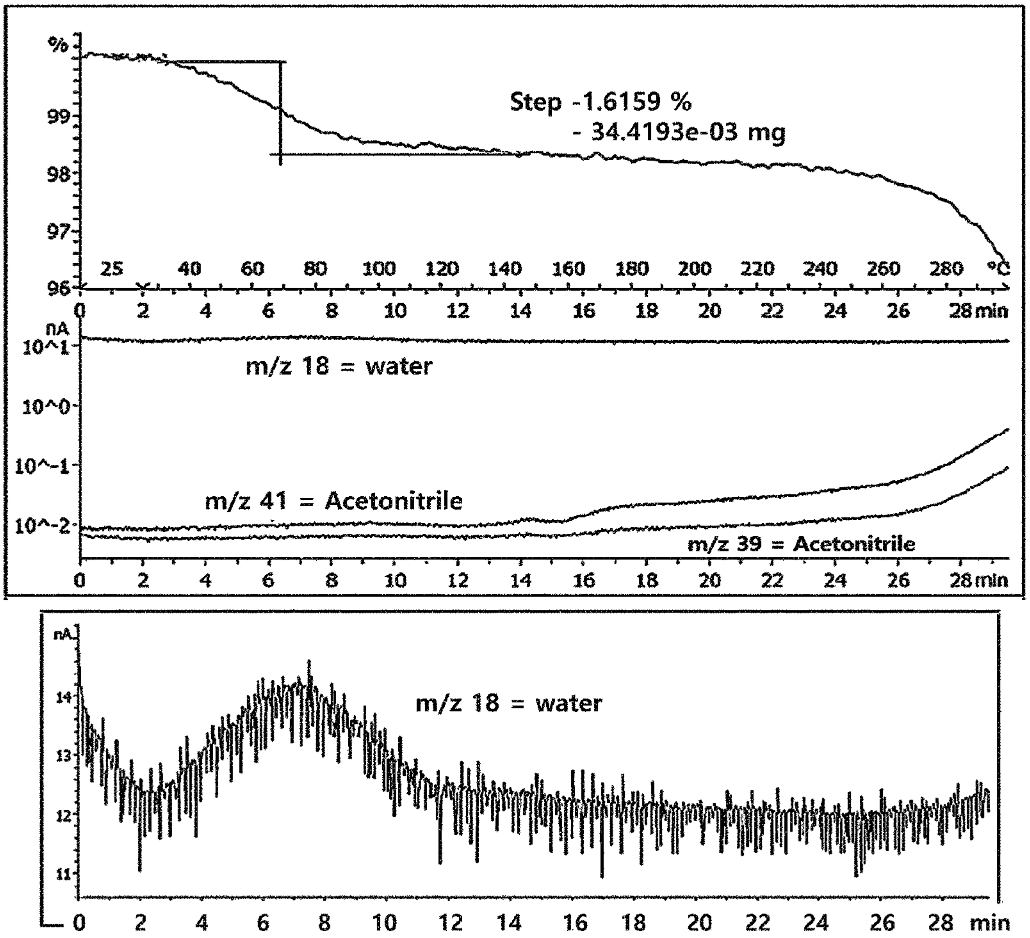
FIG. 3 is a view showing the results of TGMS analysis on the crystalline form of the present invention.

Referring to FIG. 3, as a result of thermogravimetric analysis (TGA), it can be confirmed that the crystalline form of the present invention has a mass reduction rate of 1.6% at 150° C. It can be confirmed that the crystalline form of the present invention starts thermal decomposition at about 260° C.

In addition, it can be confirmed that the crystalline form of the present invention is a non-solvated form and an anhydrous form.

The present invention has been described with reference to preferred exemplary embodiments herein, but it will be understood by those skilled in the art that the present invention may be variously changed and modified without departing from the spirit and field of the present invention, as described in the following scope of patent claims.

The invention claimed is:

1. A crystalline form of N-(4-(1-(2-cyanoacetyl)-3-methyl-1,2,3,6-tetrahydropyridin-4-yl)-1H-pyrrolo[2,3-b]pyridin-6-yl) cyclopropanecarboxamide, wherein the crystalline form shows an X-ray powder diffraction pattern comprising diffraction peaks at diffraction angle 2θ (±0.2°) values of 4.6°, 8.1°, 8.8°, 11.2°, 12.1°, 15.5°, 20.3° and 22.4°, and wherein the crystalline form shows a differential scanning calorimetry (DSC) endothermic peak at 142.07 to 157.29° C.

2. The crystalline form of claim 1, wherein the crystalline form comprises a mass reduction rate of 1.6% at 150° C. as a result of thermogravimetric analysis (TGA).

3. A method for preparing a crystalline form of N-(4-(1-(2-cyanoacetyl)-3-methyl-1,2,3,6-tetrahydropyridin-4-yl)-1H-pyrrolo[2,3-b]pyridin-6-yl) cyclopropanecarboxamide according to claim 1, the method comprising:

(A) mixing N-(4-(1-(2-cyanoacetyl)-3-methyl-1,2,3,6-tetrahydropyridin-4-yl)-1H-pyrrolo[2,3-b]pyridin-6-yl) cyclopropanecarboxamide with an organic solvent, water or a mixture thereof;

(B) stirring a resulting product obtained in above (A) to precipitate crystals at room temperature; and (C) vacuum-drying the crystal obtained in above (B) at 30° C., wherein the organic solvent is ethyl formate or acetonitrile, or a mixture thereof.

4. The method of claim 3, wherein the resulting product obtained in above (A) is a solution in which N-(4-(1-(2-cyanoacetyl)-3-methyl-1,2,3,6-tetrahydropyridin-4-yl)-1H-pyrrolo[2,3-b]pyridin-6-yl) cyclopropanecarboxamide is dissolved, or a suspension in which N-(4-(1-(2-cyanoacetyl)-3-methyl-1,2,3,6-tetrahydropyridin-4-yl)-1H-pyrrolo[2,3-b]pyridin-6-yl)cyclopropanecarboxamide is suspended.

* * * * *